United States Patent [19]

Azuma et al.

[11] Patent Number: 4,838,923
[45] Date of Patent: Jun. 13, 1989

[54] ORGANO-PHOSPHORUS COMPOUND AND HERBICIDE COMPRISING IT AS ACTIVE INGREDIENT

[75] Inventors: Shizuo Azuma; Toshiyuki Hiramatsu; Koji Nakagawa, all of Iwakuni; Yataro Ichikawa, Tokorozawa, all of Japan

[73] Assignee: Teijin Limited, Osaka, Japan

[21] Appl. No.: 26,987

[22] Filed: Mar. 17, 1987

[51] Int. Cl.$^4$ ............ C07F 9/40; C07F 9/58; A01N 43/40; A01N 57/06
[52] U.S. Cl. .................................. 71/86; 546/24; 558/170; 260/502.5 D
[58] Field of Search ........... 260/502.5 D; 558/170; 71/86; 546/24

[56] References Cited

U.S. PATENT DOCUMENTS 4,654,072  3/1987  Felix ............................. 71/86
4,685,952  8/1987  Azuma et al. ................. 71/86

Primary Examiner—Alan L. Rotman
Attorney, Agent, or Firm—Wenderoth, Lind & Ponack

[57] ABSTRACT

An organo-phosphorus compound represented by the following formula (I)

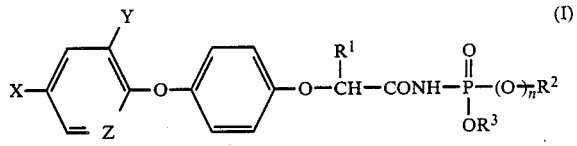

wherein X and Y are identical or different and each represents a hydrogen atom, a halogen atom, $CF_3$ or an alkyl group having not more than 5 carbon atoms; Z represents CH or N; $R^1$, $R^2$ 1 to 3 are identical or different and each represents a hydrogen atom or a lower alkyl group having 1 to 5 carbon atoms; and n is zero or 1. The compound is useful, as a herbicide, for eradicating weeds, especially narrow-leaved weeds.

8 Claims, No Drawings

ORGANO-PHOSPHORUS COMPOUND AND HERBICIDE COMPRISING IT AS ACTIVE INGREDIENT

This invention relates to an organo-phosphorus compound and a herbicide comprising it as an active ingredient. More specifically, this invention pertains to organo-phosphorus compounds which have selective herbicidal activity and selectively eradicate narrow-leaved weeds without killing narrow-leaved crop plants such as corn and rice.

Herbicides of the type which selectively kills broad-leaved weeds, typified by 2,4-dichlorophenoxyacetic acid, are known as selective herbicidally active compounds. The selectivity of the herbicidal activity of 2,4-dichlorophenoxyacetic acid is between narrow-leaved plants including crop plants and weeds and broad-leaved plants including crop plants and weeds. It is known that 2,4-dichlorophenoxyacetic acid has very little or no activity against narrow-leaved plants [see, for example, Nature, Vol. 155, page 498 (1945)]. It is known on the other hand that compounds resulting from introduction of a chloro- or trifluoromethyl-substituted phenoxy group or a chloro- or trifluoromethyl-substituted pyridyloxy group into the aromatic group of the above compound have the activity of selectively killing narrow-leaved plants.

Japanese Laid-Open Patent Publication No. 44631/1976 discloses a herbicide comprising alpha-[4-(4-trifluoromethylphenoxy)phenoxy]propionic acid, an alpha-[4-(monohalogen-substituted-4-trifluoromethylphenoxy)phenoxy]propionic acid, or a derivative thereof. This patent document specifically discloses only some alkyl esters, alkoxyalkyl esters, chloro phenyl esters, benzyl esters, amilids, acid chlorides and thioesters of the above compounds as the derivative. As shown in Table 5, for example, of this patent document, these compounds do not inhibit growth of broad-leaved plants, whether weeds or crops, but kill narrow-leaved plants such as beer barley, wheat, corn, millet, crabgrass and barnyard grass.

Japanese Laid-Open Patent Publication No. 125626/1977 discloses a herbicide comprising as an active ingredient a compound represented by the following formula

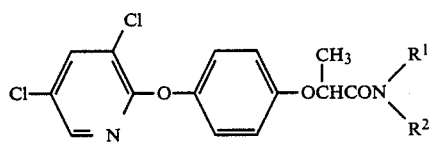

wherein $R^1$ is hydroxy, hydroxyalkyl, lower alkoxy, lower alkenyloxy, acyl, amino, aralkyl, chloroaralkyl, —$R^3$—$COOR^4$ (where $R^3$ is lower alkylene, and $R^4$ is hydrogen, lower alkyl or a salt-forming atom or radical), or

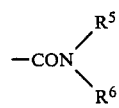

(where $R^5$ and $R^6$ are hydrogen, lower alkyl or lower alkoxy); $R^2$ is hydrogen, lower alkyl, lower alkoxy, hydroxyalkyl, phenyl, or chlorophenyl; and

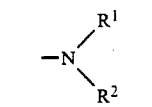

may be

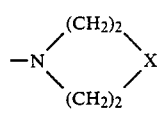

(where X is methylene or oxygen). This patent document states that the above compound hardly affects broad-leaved plants, but kill narrow-leaved plants such as barnyard grass.

Japanese Laid-Open Patent Publication No. 15,825/1977 discloses a herbicide comprising as an active ingredient a compound represented by the following formula

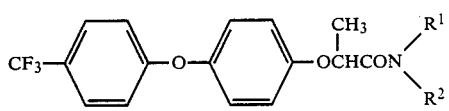

wherein $R^1$ is —$R^3$—$COOR^4$ (where $R^3$ and $R^4$ are the same as defined above), hydroxyalkyl, —$COR^5$ (where $R^5$ is lower alkyl or cycloalkyl),

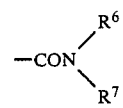

(where $R^6$ and $R^7$ are hydrogen, lower alkyl or lower alkoxy), or an aralkyl or heterocyclic group which may be substituted by at least one of halogens and lower alkyl or alkoxy groups; $R^2$ is hydrogen, lower alkyl, or phenyl which may be substituted by at least one of halogens and lower alkyl or alkoxy groups; and

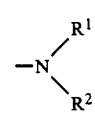

may be

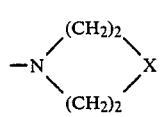

(where X is O or $CH_2$). This patent document states that the above compound hardly affects broad-leaved plants such as radish and soybeans, but shows strong activity against barnyard grass and crabgrass.

Japanese Laid-Open Patent Publication No. 2438/1978 discloses a compound of the following formula

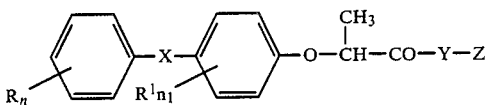

wherein R and R¹ represent halogen, $C_{1-4}$ haloalkyl, $C_{1-4}$ alkyl, nitro, $C_{1-4}$ alkoxy, or $C_{1-4}$ alkylthio, n and $n_1$ are integers of 0 to 3, X is —O— or —$CH_2$—, Y is O, S or NH, Z is cyanoethyl or

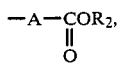

A is a methylene group substituted by $CH_3$, $C_2H_5$, $COCH_3$ or another radical represented by $COOR_3$ or a phenyl group mono- or di-substituted by $C_{1-4}$ alkyl, halogen and/or nitro, and $R^3$ is $C_{1-4}$ alkyl, and a herbicide comprising the above compound as an active ingredient. This patent document states that the above compound controls gramineous weeds such as Avena, Alopecurus, Lolium, Setaria, Echinocloa and Digitaria.

Japanese Patent Publication No. 8727/1979 describes a herbicide comprising as an active ingredient a compound of the following formula

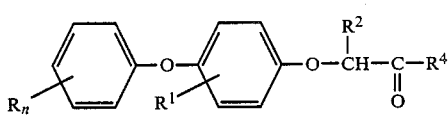

wherein R is halogen, $C_{1-4}$ alkyl, $C_{1-4}$ alkoxy or $C_{1-4}$ alkylthio, $R^1$ is H, halogen or $C_{1-4}$ alkyl, n is an integer of 1 to 3, $R^2$ is H, $C_{1-10}$ alkyl or $C_{2-6}$ alkoxyalkyl, and $R^4$ is OH, $C_{1-10}$ alkoxy, trichloroethyloxy, $C_{1-6}$ alkylthio, $C_{2-6}$ alkenyloxy, cyclohexyloxy, methylcyclohexyloxy, phenoxy substituted by one or two halogens, phenylthio which may be substituted by one or two halogens, alkylamino in which the alkyl has 1 to 4 carbon atoms, dialkylamino or

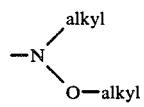

in which the alkyl has 1 to 4 carbon atoms, phenylamino substituted by halogen, $CF_3$, —$OCF_2CF_2H$ or —$COOCH_3$, or —O-Kat where Kat is an inorganic or organic base cation. This patent document states that the above herbicide has an outstanding selective herbicidal action on gramineous weeds.

European Laid-Open Patent Publication No. 0138158 describes a compound of the following formula

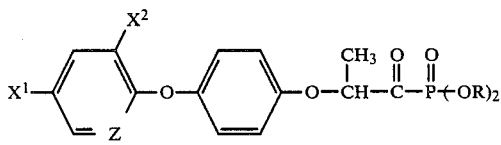

wherein $X^1$ is halogen or $CF_3$, $X^2$ is H, halogen or $CF_3$, Z is N, CH, or CCl, and R is alkyl or haloalkyl, as a total or selective herbicide for use against, for example, mono- and di-cotyledonous weeds in perennial crops or for pre- or post-emergence use against grassy weeds in cultures such as beet, cotton, soya, potatoes and cereals.

German Laid-Open Patent Publication No. 3402982 (Japanese Laid-Open Patent Publication No. 163891/1985) describes phenoxypropionyloxyalkanephosphonates of the following formula

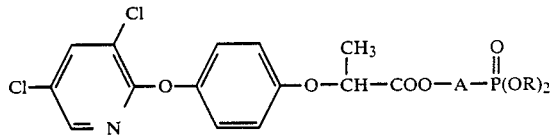

wherein R is alkyl which may be substituted and A is alkanediyl which may be substituted. This patent document discloses that these compounds are effective for killing broad-leaved or narrow-leaved weeds.

It is an object of this invention therefore to provide novel organo-phosphorus compounds.

Another object of this invention is to provide a selective herbicide having selective herbicidal activity.

Another object of this invention is to provide a selective herbicide which selectively kills narrow-leaved weeds without substantially inhibiting the growth of broad-leaved plants and substantially affecting useful narrow-leaved plants.

Another object of this invention is to provide selective herbicidal compounds which eradicate narrow-leaved weeds without substantially causing phytotoxicity to useful crop plants, particularly broad-leaved crops such as soybean, cotton, sunflower and beet and narrow-leaved crops such as corn and wheat and therefore without substantially inhibiting the growth of these useful plants; and herbicides containing the aforesaid compounds.

Another object of this invention is to provide compounds which kill many narrow-leaved plants or inhibit their growth without causing substantial phytotoxicity to narrow-leaved crops such as rice, corn and wheat and various broad-leaved crops, and therefore when applied to a locus where the aforesaid useful crops and hazardous weeds grow together, can create a condition in which the useful crops easily grow beyond the growth of the weeds.

Another object of this invention is to provide a selective herbicide applicable by foliar spraying and soil treatment, which can kill, or inhibit the growth of, weeds by application to their foliage, and also can inhibit the emergence of weeds without substantially inhibiting the emergence of useful crops by application to the soil before emergence.

Another object of this invention is to provide a selective herbicide which has low toxicity to animals and fish and remains little in the soil.

Another object of this invention is to provide a method of eradicating weeds by using the aforesaid compounds or herbicides of this invention.

Further objects of this invention along with its advantages will become apparent from the following description.

According to this invention, the objects and advantages of this invention are achieved by an organophosphorus compound represented by the following formula (I)

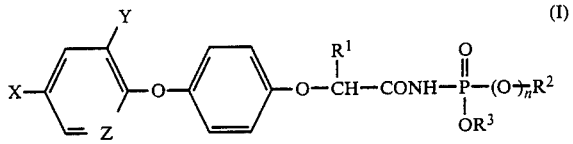

(I)

wherein X and Y are identical or different and each represents a hydrogen atom, a halogen atom, CF₃ or an alkyl group having not more than 5 carbon atoms; Z represents CH or N; R¹, R² and R³ are identical or different and each represents a hydrogen atom or a lower alkyl group having 1 to 5 carbon atoms and n is zero or 1.

In formula (I), X and Y are identical or different, and each represents a hydrogen atom, a halogen atom, CF₃ or an alkyl group having not more than 5 carbon atoms. The halogen atom is, for example, fluorine, chlorine or bromine. The alkyl group having not more than 5 carbon atoms may be linear or branched, and includes, for example, methyl, ethyl, n-propyl, iso-propyl, n-butyl, sec-butyl, iso-butyl, t-butyl and n-pentyl.

In formula (I), at least one of X and Y is preferably a halogen atom, CF₃ or an alkyl group having not more than 5 carbon atoms.

Z is CH or N, and the compounds of formula (I) may be divided into the following groups according to the definition of Z for the sake of convenience.

Compounds of formula (I) in which Z is CH are represented by the following formula

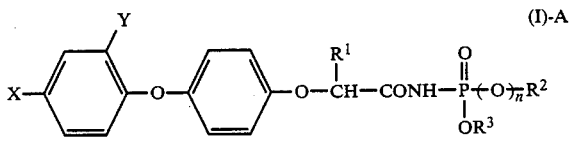

(I)-A wherein X, Y, R¹, R², R³ and n are as defined above.

Compounds of formula (I) in which Z is N are represented by the following formula

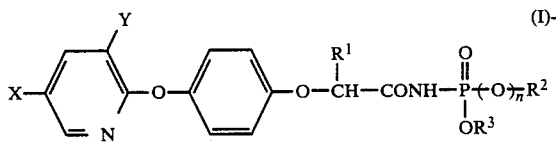

(I)-B wherein X, Y, R¹, R², R³ and n are as defined above.

In formula (I) [including formulae (I)-A and (I)-B throughout the specification], R¹, R² and R³ are identical or different, and each represents a hydrogen atom or a lower alkyl group having 1 to 5 carbon atoms and n is zero or 1. Specific examples of the alkyl group having 1 to 5 carbon atoms are the same as cited above for X and Y.

R¹ is preferably a hydrogen atom or a methyl group, especially the methyl group. R² and R³ are preferably a methyl, ethyl, propyl or butyl group.

Specific examples of the organo-phosphorus compounds of formula (I) are given below.

Compounds of formula (I)-A (100) dimethyl 2-[4-(4-trifluoromethylphenoxy)-phenoxy]propionylaminophosphonate, (102) dimethyl 2-[4-(2-chloro-4-trifluoromethyl-phenoxy)phenoxy]propionylaminophosphonate, (104) diethyl 2-[4-(4-trifluoromethylphenoxy)-phenoxy]propionylaminophosphonate, (106) diethyl 2-[4-(2-chloro-4-trifluoromethylphenoxy)phenoxy]propionylaminophosphonate, (108) dipropyl 2-[4-(4-trifluoromethylphenoxy)-phenoxy]propionylaminophosphonate, (110) dibutyl 2-[4-(4-trifluoromethylphenoxy)-phenoxy]propionylaminophosphonate, (112) methyl P-methyl-2-[4-(4-trifluoromethyl-phenoxy)phenoxy]propionylaminophosphinate, (114) ethyl P-ethyl-2-[4-(4-trifluoromethylphenoxy)-phenoxy]propionylaminophosphinate, (116) ethyl P-ethyl-2-[4-(2-chloro-4-trifluoromethyl-phenoxy)phenoxy]propionylaminophosphinate, (118) dimethyl 4-(4-trifluoromethylphenoxy)phenoxyacetylaminophosphonate.

Compounds of formula (I)-B (200) dimethyl 2-[4-(3-chloro-5-trifluoromethyl-pyridin-2-yloxy)phenoxy]propionylaminophosphonate, (202) dimethyl 2-[4-(5-trifluoromethyl-pyridin-2-yloxy)phenoxy]propionylaminophosphonate, (204) diethyl 2-[4-(3-chloro-5-trifluoromethyl-pyridin-2-yloxy)phenoxy]propionylaminophosphonate, (206) diethyl 2-[4-(5-trifluoromethyl-pyridin-2-yloxy)phenoxy]propionylaminophsophonate, (208) dipropyl 2-[4-(3-chloro-5-trifluoromethyl-pyridin-2-yloxy)phenoxy]propionylaminophosphonate, (210) dibutyl 2-[4-(3-chloro-5-trifluoromethyl-pyridin-2-yloxy)phenoxy]propionylaminophosphonate, (212) methyl P-methyl-2-[4-(3-chloro-5-trifluoromethyl-pyridin-2-yloxy)phenoxy]propionylaminophosphinate, (214) ethyl P-ethyl-2-[4-(3-chloro-5-trifluoromethyl-pyridin-2-yloxy)phenoxy]propionylaminophosphinate, (216) ethyl P-ethyl-2-[4-(5-trifluoromethyl-pyridin-2-yloxy)phenoxy]propionylaminophosphinate, (218) diethyl 4-(3-chloro-5-trifluoromethyl-pyridin-2-yloxy)phenoxyacetylaminophosphonate.

The compounds of formula (I) can be produced, for example, by process 1 or process 2 shown by the following reaction scheme.

Process 1

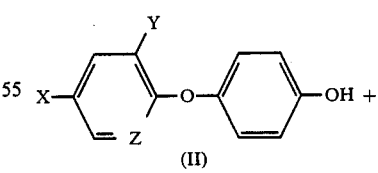

(II)

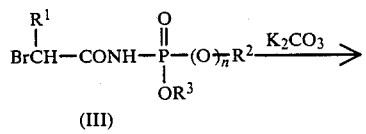

(III)

Compound of formula (I)

Process 2

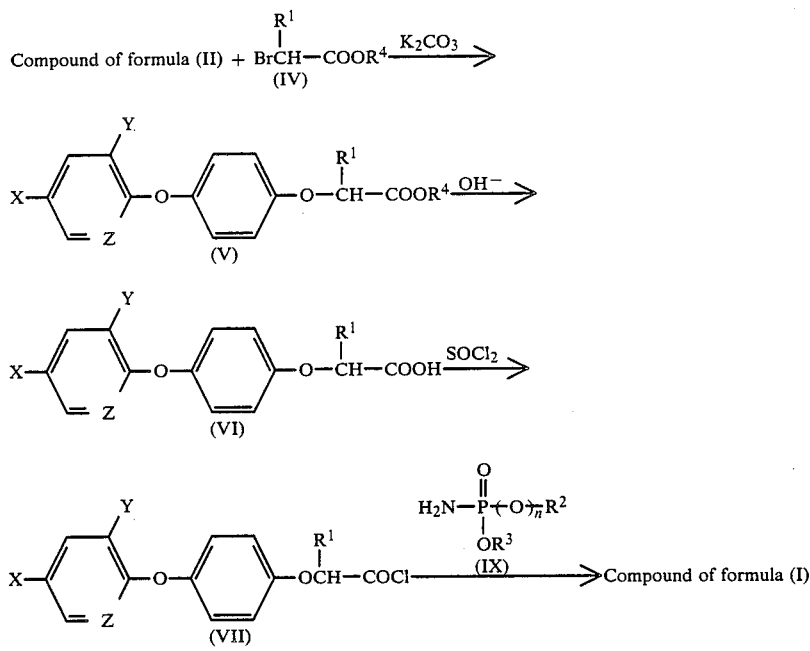

In formulae (II) to (IX) above, X, Y, Z, $R^1$, $R^2$ and $R^3$ are as defined above. $R^4$ in formulae (IV) and (V) represents an alkyl group having 1 to 5 carbon atoms.

The steps in each of processes 1 and 2 are carried out by methods known per se. When it is desired to obtain a compound of formula (I) in which $R^2$ and $R^3$ are hydrogen atoms by process 2, the above reaction is carried out by using a compound of formula (IX) in which $R^2$ and $R^3$ are hydrogen atoms; or the reaction is carried out by using a compound of formula (IX) in which $R^2$ and $R^3$ are alkyl groups having 1 to 5 carbon atoms to give a compound of formula (I) in which $R^2$ and $R^3$ are the corresponding lower alkyl groups, and the resulting compound (I) is hydrolyzed.

The organo-phosphorus compounds of formula (I) have the property of affecting the metabolism of plants to inhibit the growth of a certain kind of plants, regulate the growth of a certain kind of plants, dwarf a certain kind of plants, or to kill a certain kind of plants.

The compounds of formula (I) provided by this invention show selective herbicidal activity, and particularly have the marked property of selectively killing narrow-leaved weeds without substantially inhibiting the growth of broad-leaved plants and substantially affecting narrow-leaved useful plants.

Accordingly, the present invention also provides a herbicide comprising the organo-phosphorus compound of formula (I) as a herbicidally active ingredient.

The compounds of formula (I) provided by this invention can also be applied to seeds of plants, and to plants in various growth stages through foliage or roots. In other words, the compounds of this invention, either as such or as a composition, are applied to plants whose growth is to be inhibited, namely plants whose metabolism is to be regulated, seeds of such plants, a locus where such plants are growing, or a locus where the growth of such plants is anticipated, in amounts sufficient to regulate the metabolism of the plants.

The metabolism of plants can be regulated by applying the compounds of this invention at a rate of 1 g to 2 kg, preferably 2 g to 1 kg, especially preferably 5 g to 200 g, per 10 ares.

When it is desired to inhibit the growth of, or eradicate, hazardous plants by the compounds of this invention, the compounds, either as such or as a composition, can be applied directly to the plants or their seeds or to the soil in amounts sufficient to inhibit the growth of, or eradicate, the plants in a locus where beneficial plants or their seeds and the hazardous plants or their seeds are growing together or are likely to grow together.

The hazardous plants may be defined as plants which come into an environment created by man, such as a paddy or an upland farm, from the surrounding nature, and grow there and which are considered by man to be useless in that environment or do harm to its. Such hazardous plants are generally called weeds. Examples of the weeds to which the compounds of this invention are to be applied are shown below.

Sorghum halepense,
Avena fatua,
Digitaria adscendens,
Setaria faberi,
Agropyron repens,
Panicum texanum,
Echinochloa crus-galli,
Setaria viridis,
Poa annua,
Eleusine indica,
Axonopus affinis,
Bachiaria platyphylla,
Bromus tectorum,
Cynodon dactylon,
Panicum dichotomiflorum,
Paspalum dilatatum,
Echiochloa colona,
Panicum capillare, and
Setaria lutescens.

The beneficial plants in the above case are, for example, plants producing cereals, and lawns. Since the compounds of this invention exert little or no adverse effect on the growth of not only various broad-leaved plants such as soybean, cotton, sunflower and beet but also harrow-leaved crops such as rice, corn and wheat, they are very suitable for application to paddies and upland farms for cultivating these plants. By applying the compounds of this invention to a locus where lawns are growing, the emergence and growth of weeds can be inhibited.

In some cases, it is desirable to apply the compounds of this invention while hazardous plants do not grow so much, particularly while the height of the hazardous plants is lower, or a little bit higher, than the height of beneficial plants.

When weeds are to be eradicated by using the compounds of this invention, the compounds can be applied either as such or as a composition to weeds to be eradicated, their seeds, or a locus where such weeds are growing, or are likely to grow, for example in a crop cultivating area, in amounts sufficient for eradication.

The herbicide of this invention shows a very good effect against narrow-leaved weeds. When used in dosages which exhibit this effect, the herbicide does not substantially injure the aforesaid useful crops.

A group of preferred compounds of formula (I) which have especially good selective herbicidal activity are expressed by the following formula (I)-1

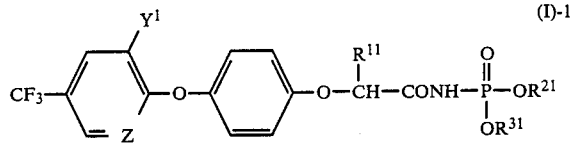

wherein Z is as defined above, $Y^1$ represents H or Cl, $R^{11}$ is identical or different and represents H or $CH_3$, and $R^{21}$ and $R^{31}$ are identical or different and each represents an alkyl group having 1 to 4 carbon atoms.

The compounds of this invention can be used in usual formulations such as a solution, an emulsifiable concentrate, a suspension, a dust, a paste or granules.

Such formulations are prepared by using at least one agriculturally acceptable diluent. Examples include solid carriers such as talc, bentonite, clay, kaolin, diatomaceous earth, white carbon, vermiculite, slaked lime, ammonium sulfate and urea; liquid carriers such as water, alcohols, dioxane, acetone, xylene, cyclohexane, methylnaphthalene, dimethylformamide, N-methylpyrrolidone, dimethyl sulfoxide, cyclohexanone, methyl ethyl ketone and methyl isobutyl ketone; surface-active agents, emulsifiers or dispersants such as alkylsulfuric acid esters, alkylsulfonic acid salts, ligninsulfonic acid salts, polyoxyethylene glycol ethers, polyoxyethylene alkylaryl ethers, polyoxyethylene sorbitan monoalkylates and dinaphthylmethanedisulfonic acid salts; and various adjuvants such as carboxylmethyl cellulose and gum arabic.

For example, such a formulation can be prepared by mixing the compound of this invention with the aforesaid carrier and/or emulsifier, etc.

The compound of this invention may be present in a proportion of usually 0.01 to 99% by weight, preferably 0.1 to 95% by weight, in the formulation.

The compound of this invention, as such or in admixture with another active compound or as the aforesaid formulation, can be applied to plants by usual methods such as spraying, atomizing, or dusting.

The following examples illustrate the present invention in greater detail.

In these examples, parts are by weight unless otherwise specified. The herbicidal activity of the active test compounds are evaluated on a scale of 0 to 5 in which 0 means that the plants were as sound as before the application of the active compound and 5 means that the application of the active compound caused the plants to wither and die, and 1, 2, 3 and 4 mean varying degrees of the enfeebled state of the plants between 0 and 5.

Production Examples

EXAMPLE 1

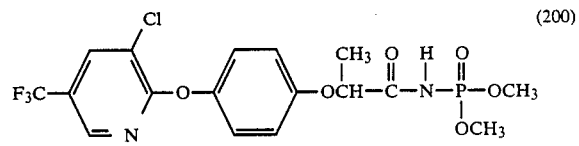

Metallic sodium (0.28 part) was added to 50 parts by volume of dry methanol, and further 1.5 parts of dimethyl aminophosphonate was added to form a solution. Methanol was removed from the solution under reduced pressure, and 20 parts by volume of tetrahydrofuran was added to the residue. A solution of 3.8 parts of 2-[4-(3-chloro-5-trifluoromethyl-pyridin-2-yloxy)-phenoxy]propionyl chloride in 10 parts by volume of tetrahydrofuran was added dropwise to the mixture. The resulting mixture was stirred at room temperature for about 5 hours, and then tetrahydrofuran was removed under reduced pressure. Ethyl acetate (50 parts by volume) was added to the residue, and the solution was washed with water (30 parts by volume×3). The organic layer was dried over anhydrous sodium sulfate, and the solvent was removed under reduced pressure. Twenty parts by volume of ether was added to the residue, and the resulting precipitate was collected by filtration and washed with ether to give 0.15 part of the captioned compound (200). This compound had a melting point of 137.0° to 137.5° C. Its IR and NMR spectral data are shown in Table 1.

EXAMPLE 2

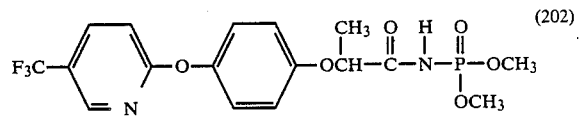

Example 1 was repeated except that 3.4 parts of 2-[4-(5-trifluoromethyl-pyridin-2-yloxy)phenoxy]propionyl chloride was used instead of 2-[4-(3-chloro-5-trifluoromethyl-pyridin-2-yloxy)phenoxy]propionyl chloride. The captioned compound (202) was obtained in an amount of 0.15 parts. This compound had a melting point of 76° to 77° C., and its IR and NMR spectral data are shown in Table 1.

EXAMPLE 3

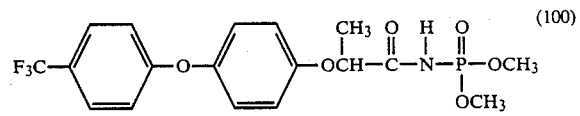

Example 1 was repeated except that 3.4 parts of 2-[4-(4-trifluoromethylphenoxy)phenoxy]propionyl chloride was used instead of 2-[4-(3-chloro-5-trifluoromethyl-pyridin-2-yloxy)phenoxy]propionyl chloride. The captioned compound (100) was obtained in an amount of 0.16 part. This compound had a melting point of 102.0° to 102.5° C., and its IR and NMR spectral data are shown in Table 1.

EXAMPLE 4

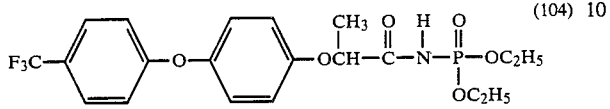

Thionyl chloride (4.4 parts by volume) was added to 3.26 parts of 2-[4-(4-trifluoromethylphenoxy)phenoxy]-propionic acid, and the mixture was refluxed for 3 hours. After the reaction, the excess of thionyl chloride was removed under reduced pressure to give 2-[4-(4-trifluoromethylphenoxy)phenoxy]propionyl chloride. A solution of the resulting propionyl chloride in 10 parts by volume of ether was added dropwise under ice cooling to a solution of 3.34 parts of diethyl aminophosphonate in 20 parts by volume of ether. Ten minutes later, 1 part by volume of triethylamine was added dropwise. After the addition, the mixture was stirred at room temperature for 3 hours. The reaction mixture was washed with water, a saturated aqueous solution of sodium bicarbonate and water in this order. The organic layer was dried over anhydrous sodium sulfate, and concentrated under reduced pressure to give 2.6 parts of a crude product. The crude product was recrystallized from ethyl acetate/ether to give 1.1 parts of the captioned compound. This compound had a melting point of 134.5° to 135° C., and its IR and NMR spectral data are shown in Table 1.

EXAMPLE 5

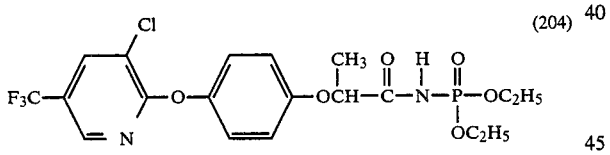

Example 4 was repeated that 3.62 parts of 2-[4-(3-chloro-5-trifluoromethyl-pyridin-2-yloxy)phenoxy]propionic acid was used instead of 2-[4-(4-trifluoromethyl-phenoxy)phenoxy]propionic acid was used. The captioned compound (204) was obtained in an amount of 0.16 part. This compound had a melting point of 140° to 141° C., and its IR and NMR spectral data are shown in Table 1.

EXAMPLE 6

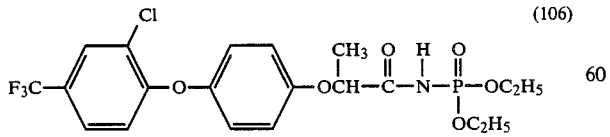

Example 4 was repeated except that 3.6 parts of 2-[4-(2-chloro-4-trifluoromethyphenoxy]propionic acid was used instead of 2-[4-(4-trifluoromethylphenoxy)phenoxy]propionic acid was used. The captioned compound (106) was obtained in an amount of 1.5 parts. This compound had a melting point of 95° to 96° C., and its IR and NMR spectral data are shown in Table 1.

EXAMPLE 7

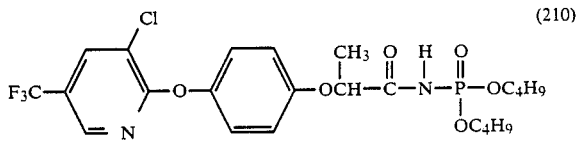

Example 5 was repeated except that 4.56 parts of dibutyl aminophosphonate was used instead of diethyl aminophosphonate. There was obtained 1.7 parts of the captioned compound (210). The IR and NMR spectal data of this compound are shown in Table 1.

EXAMPLE 8

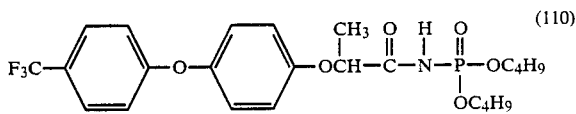

Example 4 was repeated except that 4.56 parts by dibutyl aminophosphonate was used instead of diethyl aminophosphonate. There was obtained 1.0 part of the captioned compound (110). The IR and NMR spectral data of this compound are shown in Table 1.

EXAMPLE 9

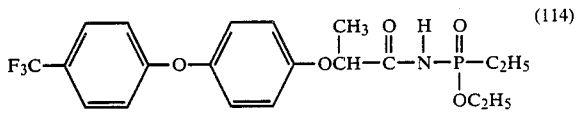

A solution of 3.3 parts of 2-[4-(4-trifluoromethyl-phenosy)phenoxy]propionyl chloride synthesized in Example 4 in 10 parts by volume of ether was added dropwise under ice cooling to a solution of 1.65 parts of ethyl P-ethylphosphoramidate in 20 parts by volume of ether. Ten minutes later, 1 part by volume of triethylamine was added. After the addition, the mixture was reacted at room temperature for 3 hours. After the reaction, the reaction mixture was washed with water, a saturated aqueous solution of sodium bicarbonate, and water in this order. The organic layer was dried over anhydrous sodium sulfate and concentrated under reduced pressure. The crude product was purified by silica gel column chromatography to give 0.9 part of the captioned compound (114). The IR and NMR spectral data of the compound are shown in Table 1.

EXAMPLE 10

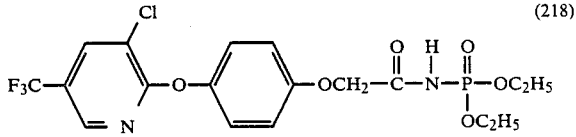

Example 5 was repeated except that 4-(3-chloro-5-trifluoromethyl-pyridin-2-yloxy)phenoxyacetic acid was used instead of 2-[4-(3-chloro-5-trifluoromethyl-pyridin-2-yloxy)phenoxy]propinic acid. There was obtained 1.5 parts of the captioned compound (218). The IR and NMR spectral data of this compound are shown in Table 1.

TABLE 1

$$\text{X}\underset{\text{Z}}{\overset{\text{Y}}{\bigcirc}}-\text{O}-\bigcirc-\text{OCH}\underset{\text{R}^1}{-}\underset{\text{O}}{\overset{\text{O}}{\text{C}}}-\text{N}\underset{\text{H}}{-}\underset{\text{OR}^3}{\overset{\text{O}}{\text{P}}}-(\text{O})_n\text{R}^2$$

| Example | Compound No. | X | Y | Z | R¹ | R² | R³ | n | IR ν(cm⁻¹) | NMR in CDCl₃ δ (ppm) | |
|---|---|---|---|---|---|---|---|---|---|---|---|
| 1 | 200 | —CF₃ | —Cl | =N— | —CH₃ | —CH₃ | —CH₃ | 1 | 3100 | 1.60 | (3H) |
|   |   |   |   |   |   |   |   |   | 1700 | 3.67–3.93 | (6H) |
|   |   |   |   |   |   |   |   |   | 1600 | 4.70 | (1H) |
|   |   |   |   |   |   |   |   |   | 1500 | 6.83–7.67 | (5H) |
|   |   |   |   |   |   |   |   |   | 1320 | 7.93 | (1H) |
|   |   |   |   |   |   |   |   |   | 1240 | 8.21 | (1H) |
| 2 | 202 | —CF₃ | —H | =N— | —CH₃ | —CH₃ | —CH₃ | 1 | 3100 | 1.58 | (3H) |
|   |   |   |   |   |   |   |   |   | 1705 | 3.65–3.93 | (6H) |
|   |   |   |   |   |   |   |   |   | 1610 | 4.68 | (1H) |
|   |   |   |   |   |   |   |   |   | 1500 | 6.81–7.93 | (7H) |
|   |   |   |   |   |   |   |   |   | 1325 | 8.20 | (1H) |
|   |   |   |   |   |   |   |   |   | 1235 |  |  |
|   |   |   |   |   |   |   |   |   | 1040 |  |  |
| 3 | 100 | —CF₃ | —H | =CH— | —CH₃ | —CH₃ | —CH₃ | 1 | 3100 | 1.60 | (3H) |
|   |   |   |   |   |   |   |   |   | 1700 | 3.68–3.95 | (6H) |
|   |   |   |   |   |   |   |   |   | 1610 | 4.68 | (1H) |
|   |   |   |   |   |   |   |   |   | 1500 | 6.85–7.62 | (9H) |
|   |   |   |   |   |   |   |   |   | 1330 |  |  |
|   |   |   |   |   |   |   |   |   | 1235 |  |  |
|   |   |   |   |   |   |   |   |   | 1050 |  |  |
| 4 | 104 | —CF₃ | —H | =CH— | —CH₃ | —C₂H₅ | —C₂H₅ | 1 | 3100 | 1.17–1.47 | (6H) |
|   |   |   |   |   |   |   |   |   | 1700 | 1.50–1.63 | (3H) |
|   |   |   |   |   |   |   |   |   | 1610 | 3.87–4.33 | (4H) |
|   |   |   |   |   |   |   |   |   | 1500 | 4.43–4.80 | (1H) |
|   |   |   |   |   |   |   |   |   | 1320 | 6.80–7.57 | (9H) |
|   |   |   |   |   |   |   |   |   | 1230 |  |  |
|   |   |   |   |   |   |   |   |   | 1040 |  |  |
| 5 | 204 | —CF₃ | —Cl | =N— | —CH₃ | —C₂H₅ | —C₂H₅ | 1 | 3100 | 1.20–1.47 | (6H) |
|   |   |   |   |   |   |   |   |   | 1700 | 1.53–1.67 | (3H) |
|   |   |   |   |   |   |   |   |   | 1600 | 3.97–4.30 | (4H) |
|   |   |   |   |   |   |   |   |   | 1500 | 4.47–4.83 | (1H) |
|   |   |   |   |   |   |   |   |   | 1320 | 6.77–7.67 | (5H) |
|   |   |   |   |   |   |   |   |   | 1240 | 7.87–8.17 | (2H) |
|   |   |   |   |   |   |   |   |   | 1040 |  |  |
| 6 | 106 | —CF₃ | —Cl | =CH— | —CH₃ | —C₂H₅ | —C₂H₅ | 1 | 3100 | 1.23–1.76 | (9H) |
|   |   |   |   |   |   |   |   |   | 1700 | 3.93–4.47 | (4H) |
|   |   |   |   |   |   |   |   |   | 1600 | 4.50–4.86 | (1H) |
|   |   |   |   |   |   |   |   |   | 1500 | 6.83–7.83 | (8H) |
|   |   |   |   |   |   |   |   |   | 1325 |  |  |
|   |   |   |   |   |   |   |   |   | 1240 |  |  |
|   |   |   |   |   |   |   |   |   | 1040 |  |  |
| 7 | 210 | —CF₃ | —Cl | =N— | —CH₃ | —C₄H₉ | —C₄H₉ | 1 | 3100 | 0.83–1.10 | (6H) |
|   |   |   |   |   |   |   |   |   | 1705 | 1.10–1.86 | (11H) |
|   |   |   |   |   |   |   |   |   | 1600 | 3.93–4.33 | (4H) |
|   |   |   |   |   |   |   |   |   | 1500 | 4.53–4.90 | (1H) |
|   |   |   |   |   |   |   |   |   | 1325 | 6.83–7.60 | (5H) |
|   |   |   |   |   |   |   |   |   | 1245 | 7.98 | (1H) |
|   |   |   |   |   |   |   |   |   |  | 8.27 | (1H) |
| 8 | 110 | —CF₃ | —H | =CH— | —CH₃ | —C₄H₉ | —C₄H₉ | 1 | 3100 | 0.80–1.07 | (6H) |
|   |   |   |   |   |   |   |   |   | 1700 | 1.13–1.80 | (11H) |
|   |   |   |   |   |   |   |   |   | 1610 | 3.90–4.33 | (4H) |
|   |   |   |   |   |   |   |   |   | 1500 | 4.47–4.81 | (1H) |
|   |   |   |   |   |   |   |   |   | 1320 | 6.87–7.60 | (9H) |
|   |   |   |   |   |   |   |   |   | 1230 |  |  |
| 9 | 114 | —CF₃ | —H | =CH— | —CH₃ | —C₂H₅ | —C₂H₅ | 0 | 3100 | 0.83–1.53 | (6H) |
|   |   |   |   |   |   |   |   |   | 1700 | 1.57–1.68 | (3H) |
|   |   |   |   |   |   |   |   |   | 1610 | 1.83–2.40 | (2H) |
|   |   |   |   |   |   |   |   |   | 1500 | 3.80–4.33 | (2H) |
|   |   |   |   |   |   |   |   |   | 1320 | 4.50–4.83 | (1H) |
|   |   |   |   |   |   |   |   |   | 1220 | 6.80–7.60 | (9H) |
| 10 | 218 | —CF₃ | —Cl | =N— | —H | —C₂H₅ | —C₂H₅ | 1 | 3100 | 1.27–1.50 | (6H) |
|   |   |   |   |   |   |   |   |   | 1720 | 4.00–4.48 | (4H) |
|   |   |   |   |   |   |   |   |   | 1610 | 4.53 | (2H) |
|   |   |   |   |   |   |   |   |   | 1500 | 6.86–7.86 | (5H) |
|   |   |   |   |   |   |   |   |   | 1320 | 7.93 | (1H) |
|   |   |   |   |   |   |   |   |   | 1230 | 8.21 | (1H) |

FORMULATION EXAMPLE

One part of the active compound of this invention was added to 5,000 parts of a mixture of acetone and water (1:1 by volume), and 2.6 parts of a nonionic surfactant (Sorpol 2680, tradename) was added to form a solution.

TEST EXAMPLE 1

A solution of the active compound of the invention was prepared in accordance with the above Formulation Example.

Seeds of plants were sown in the soil, and after germination, cultivated for 2 to 3 weeks.

The prepared solution was applied to these plants at the rate of application indicated in Tables 2 and 3. Thereafter, the plants were continued to be cultivated for 3 weeks without applying the above solution. The results are given in Tables 2 and 3.

TEST EXAMPLE 2

Seeds of plants to be evaluated were sown in the soil, and on the second day after sowing, were treated as follows and the growth of the plants was observed for 3 weeks.

A solution of the active compound of the invention was uniformly applied at the rate of application indicated in Table 4 to the surface of the soil after the sowing. Thereafter, the plants were continued to be cultivated without applying the active compound solution. The results are shown in Table 4.

The alphabets given in the column of "Plant" in Tables 2, 3 and 4 represent the following plants.

A: *Sorghum halepense*
B: *Avena fatua*
C: *Digitaria adsendens*
D: *Eleusine indica*
E: *Setaria faberi*
F: *Setaria viridis*
G: *Agropyron repens*
H: *Panicum texanum*
I: *Poa annua*
J: *Echinochloa crus-galli*
K: Soybean
L: Corn

TABLE 2

| Compound No. | Rate of application (g/10a) | A | B | C | D | E | F | G | H | I | J | K |
|---|---|---|---|---|---|---|---|---|---|---|---|---|
| (200) | 25 | 5 | 5 | 5 | 5 | 5 | 5 | 5 | 5 | 5 | 5 | 0 |
|  | 6.3 | 5 | 3 | 5 | 5 | 5 | 5 | 3 | 5 | 5 | 5 | 0 |
| (202) | 25 | 5 | 4 | 5 | 5 | 5 | 5 | 4 | 5 | 5 | 5 | 0 |
|  | 12.5 | 5 | 2 | 5 | 5 | 5 | 4 | 3 | 5 | 5 | 4 | 0 |
| (100) | 25 | 5 | 5 | 5 | 5 | 5 | 5 | 4 | 5 | 5 | 5 | 0 |
|  | 6.3 | 4 | 2 | 5 | 4 | 5 | 4 | 2 | 5 | 5 | 5 | 0 |

TABLE 3

| Compound No. | Rate of application (g/10 a) | C | F | A | K | L |
|---|---|---|---|---|---|---|
| (104) | 50 | 5 | 5 | 5 | 0 | 1 |
|  | 25 | 5 | 4 | 4 | 0 | 1 |
| (204) | 25 | 5 | 5 | 5 | 0 | 2 |
|  | 12.5 | 5 | 4 | 5 | 0 | 1 |
| (106) | 50 | 5 | 5 | 4 | 0 | 2 |
|  | 25 | 5 | 4 | 3 | 0 | 1 |
| (210) | 100 | 5 | 3 | 4 | 0 | 0 |
| (110) | 100 | 4 | 4 | 3 | 0 | 0 |
| (114) | 50 | 5 | 5 | 5 | 0 | 2 |
|  | 25 | 5 | 4 | 4 | 0 | 1 |

TABLE 3-continued

| Compound No. | Rate of application (g/10 a) | C | F | A | K | L |
|---|---|---|---|---|---|---|
| (218) | 100 | 3 | 3 | 3 | 0 | 0 |

TABLE 4

| Compound No. | Rate of application (g/10 a) | C | F | A | K | L |
|---|---|---|---|---|---|---|
| (200) | 50 | 5 | 5 | 5 | 0 | 2 |
|  | 25 | 5 | 5 | 5 | 0 | 0 |
| (202) | 50 | 3 | 3 | 5 | 0 | 1 |
| (104) | 100 | 5 | 4 | — | 0 | 1 |
|  | 50 | 5 | 3 | — | 0 | 0 |
| (204) | 50 | 5 | 5 | — | 0 | 2 |
| (114) | 100 | 5 | 5 | — | 0 | 1 |
|  | 50 | 5 | 3 | — | 0 | 0 |

What is claimed is:

1. An organo-phosphorus compound represented by the following formula (I)

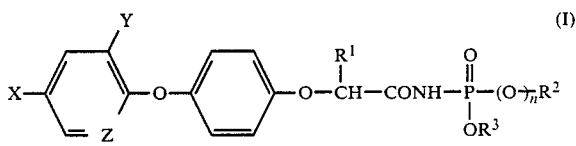

wherein X and Y are identical or different and each represents a hydrogen atom, a halogen atom, $CF_3$ or an alkyl group having not more than 5 carbon atoms; Z represents CH or N; $R^1$, $R^2$ and $R^3$ are identical or different and each represents a hydrogen atom or a lower alkyl group having 1 to 5 carbon atoms and n is zero or 1.

2. The organo-phosphorus compound of claim 1 which is represented by the following formula (I)-A

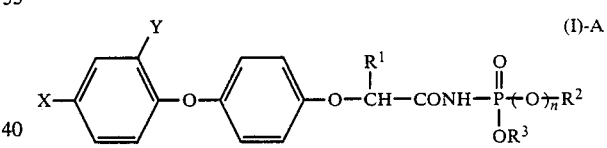

wherein X, Y, $R^1$, $R^2$, $R^3$ and n are as defined.

3. The organo-phosphorus compound of claim 1 which is represented by the following formula (I)-B

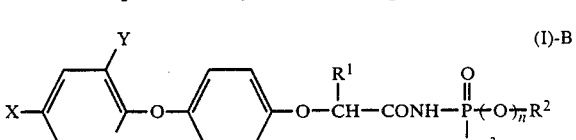

wherein X, Y, $R^1$, $R^2$, $R^3$ and n are as defined.

4. A method of eradicating weeds, which comprises applying the organo-phosphorus compounds of formula (I) according to claim 1 to a locus where narrow-leaved weeds are growing or are likely to grow in an amount effective for eradicating the weeds.

5. The method of claim 4 wherein the locus is a locus where a crops is cultivated, and the crop is either a broad-leaved or narrow-leaved plant.

6. A herbicidal composition comprising a herbicidally effective amount of an organo-phosphorus compound according to claim 1 in association with an agriculturally acceptable diluent.

7. A composition according to claim 6 wherein the herbicidally active ingredient is an organo-phosphorus compound according to claim 2.

8. A composition according to claim 6 wherein the herbicidally active ingredient is an organo-phosphorus compound according to claim 3.

* * * * *